United States Patent
Davidovich

[19]

[11] Patent Number: 6,050,817
[45] Date of Patent: Apr. 18, 2000

[54] MODEL DIE EJECTOR

[75] Inventor: Boris Davidovich, Flushing, N.Y.

[73] Assignee: S. Lekhovitser, Flushing, N.Y.

[21] Appl. No.: 09/360,986

[22] Filed: Jul. 26, 1999

[51] Int. Cl.$^7$ .................................................. A61C 19/00
[52] U.S. Cl. .................................................................. 433/74
[58] Field of Search ............................... 433/74, 141, 164

[56] References Cited

U.S. PATENT DOCUMENTS

| | | | |
|---|---|---|---|
| D. 303,709 | 9/1989 | Roden | D24/16 |
| D. 303,836 | 10/1989 | Roden | D24/16 |
| 3,553,839 | 1/1971 | Gores | 433/74 |
| 3,896,548 | 7/1975 | Zahn | 433/74 |
| 4,174,570 | 11/1979 | Schwartz | 433/74 |
| 4,205,443 | 6/1980 | Weissman | 433/74 |
| 4,242,812 | 1/1981 | Randoll et al. | 433/74 |
| 4,457,709 | 7/1984 | Moore | 433/74 |
| 4,459,110 | 7/1984 | Jackson | 433/74 |
| 4,479,780 | 10/1984 | Gores | 433/74 |
| 4,801,264 | 1/1989 | Weissman | 433/74 |
| 4,954,081 | 9/1990 | Williams | 433/53 |
| 5,222,891 | 6/1993 | Poveromo | 433/74 |
| 5,242,302 | 9/1993 | Riehm | 433/164 |
| 5,286,191 | 2/1994 | Poveromo | 433/74 |
| 5,342,696 | 8/1994 | Eidenbenz | 428/542.8 |
| 5,927,978 | 7/1999 | Muller | 433/141 |

*Primary Examiner*—Todd E. Manahan
*Attorney, Agent, or Firm*—Boris Leschinsky

[57] ABSTRACT

A dental model die ejector tool is designed to loosen the individual model dies mounted on a model base with a tapered dowel pin extending through the base, but at the same time not to lift them for any substantial distance. In turn, that loosening step allows for further easy separation of all the model dies with a wax cast as a single unit from the model base for further individual removal of the model dies. At one end, the model die ejector contains a pushing rod equipped with an ejector shank having a length of less than 1 mm and preferably about 0.1 mm for pushing the dowel pin upwardly in the corresponding sleeve for a short distance equal to the length of the shank so that the wax cast is not disturbed but the dowel pin is loosened. On the other end, the die ejector contains another pushing rod with an ejector cavity for loosening another commonly used type of a dowel pin extending from its sleeve after the removal of a protective cap. The depth of the cavity is sufficient to loosen the dowel pin while using the die ejector but not to lift it thus preventing any potential distortion of the wax cast.

14 Claims, 3 Drawing Sheets

MODEL DIE EJECTOR

BACKGROUND OF THE INVENTION

1. Field of the Invention

The present invention relates generally to dentistry and particularly to fabrication by dental technicians of dental models for bridges, splints and the like.

2. Description of the Prior Art

In fabricating a dental bridge, it is common for a dentist to prepare teeth that are to receive the bridge by grinding the teeth to a generally upwardly tapered shape. A impression of the prepared teeth is then made by the dentist and typically sent to a dental technician for fabrication of a bridge to fit the prepared teeth. The technician usually fills the impression with gypsum or another similar material to form a plaster cast of the patient's teeth and a set of parallel typically tapered metal dowel pins is then secured in the bottom of the cast with each individual pin underlying each prepared tooth and encased in an individual sleeve. The cast is then mounted atop a wet plaster base with the parallel pins extending through the base. According to one commonly used technique, when the base dries, the bottom of the base is buffed or sanded so that the pin ends are flush with the base bottom. According to another technique, some other pin and sleeve designs contain a removable cap at the bottom of each sleeve so that the removal of the cap exposes the lower part of the pin. The cast is then cut into segments called working model dies with a small saw with each segment or die bearing a cast of a prepared tooth. The model dies can thus be individually removed from the base by pressing their corresponding dowel pins upwardly from the bottom of the base. The segmented cast mounted to the base is then usually covered with wax to form a pattern wax cast copying the pattern of the teeth. When this wax pattern dries, the segmented waxed cast can be separated from the base by either pulling it manually off the set of dies or, alternately, by pressing the tapered dowel pins upwardly from the bottom of the base after which the individual working dies can be removed with the wax from the base as a unit for subsequent individual separation with the resulting wax pattern being used to cast a bridge or a crown. The second method is much more accurate since it avoids a potential distortion in the wax cast resulting from the fact that individual teeth may have converging central axis directions so that removal of a single piece wax cast is geometrically impossible without warping.

Up until the present time, the tapered dowel pins have been pressed from the base by hand to separate the waxed cast from the base using a sharp object. Since wax material remains somewhat soft, in some instances the pins are not dislodged from the holes in the base simultaneously, so that the second potential problem with wax cast removal arises in that some of the working dies are separated from the base before others which consequently results in distortion or warping of the wax pattern and creating a defect known as "open margins". A bridge cast from such a distorted pattern also bears the distortion such that it might not fit the patient's teeth properly. In this event, a new bridge often must be fabricated from scratch. Since it is difficult to determine that a pattern has been warped until the finished bridge is completed, many hours of tedious work molding the bridge from the warped impression is sometimes sacrificed.

There are many U.S. patents in the prior art relating to means for positioning and removal of the dowel pin when making a dental model. U.S. Pat. No. 2,851,728 shows a dental dowel pin having a single hole therein for receiving an elongated, rod-like repositioning gauge supported in the base stone of a dental model. The single rod-like gauge passes through more than one dowel pin, a construction which has limited practical value compared to an individual locking device for each dowel pin.

U.S. Pat. Nos. 3,413,725; 3,454,256; and 3,521,354 merely disclose dowel positioning systems, and also show the use of channel forming members located on the end of a dowel pin to form a channel in the base stone for facilitating the removal of a selected tooth die from the stone.

U.S. Pat. No. 4,457,709 shows a coiled wire rod for holding a dowel-pin in position in a dental cavity of a tooth impression during the pouring of dental die casting material into the cavity.

U.S. Pat. No. 3,896,548 shows a dental model provided with horizontal wedges which are inserted in mating sockets spanning the parting lines between adjacent tooth dies for maintaining alignment of the tooth dies within the model.

U.S. Pat. Nos. 4,056,585 and 4,139,943 show dowel pin constructions for use in a dental die.

U.S. Pat. No. 4,997,370 describes a two-piece metal dowel pin which prevents rotation of a tooth die but having an index which is invisible after the model has been trimmed.

U.S. Pat. Nos. 5,222,891 and 5,286,191 as well as Des. 303,709 and Des. 303,836 describe a dowel pin having a horizontally extending member available for aiding in die removal process. Although a useful addition, it still does not address the main problem which is a need for a simultaneous release of all dies together with a wax cast as a single unit.

U.S. Pat. No. 5,342,696 depicts a blank for a production of a dental mould part such as a crown and alike and discloses a an ejecting rod for separating the blank from the engagement groove secured by a biased ball member.

Finally, U.S. Pat. No. 4,954,081 discloses an apparatus and a method for dowel pin removal containing a movable base holding plate and a set of ejecting pins positionable under the dowel pin arrangement of the dental model. Once all ejecting pins are in place, the apparatus contains provisions allowing for lowering the base onto the set of ejecting pins thus causing model dies to separate from the base all at the same time. This apparatus is definitely useful in solving the above mentioned problem. However, correct positioning of all ejecting pins is a complicated and time consuming procedure. Complexities of design, setting up and using of this device would limit its applicability and wide spread use.

A long felt and unaddressed need still exists, therefore, for a simple hand tool die ejector aiding in simultaneous separating of the waxed dies in a dental cast from their plaster base such that the resulting wax pattern does not become warped or distorted with open margins. It is to the provision of such a die ejector tool that the present invention is primarily directed.

SUMMARY OF THE INVENTION

Accordingly, it is an object of the present invention to overcome these and other drawbacks of the prior art by providing a novel model die ejector tool allowing for loosening and simultaneous separation of the model dies from the model base.

It is another object of the present invention to provide a model die ejector tool allowing individual loosening but not substantial lifting of each model die from the model base thus facilitating a complete separation of the wax cast and all the model dies from the base as a single unit.

It is a further object of the invention to provide a model die ejector allowing for lifting of an individual dowel pin for a predetermined limited distance, generally not exceeding about 0.1 mm.

It is a further yet object of the invention to provide a model die ejector capable of loosening the dowel pin off the surface of the model base in such condition as when the pin lower edge is flush with the base surface when fully seated in its sleeve.

It is a further yet object of the present invention to provide a model die ejector capable of lifting the dowel pin off its seat in a sleeve in a situation where the pin/sleeve design include a removable cap so that there is space formed between the pin and the base model when the cap is removed.

According to the invention, the tapered nature of the dowel pin and sleeve design is utilized to loosen the dowel pin in the sleeve but not lift it to any substantial distance. It was empirically discovered that in order to break the tight fit between most commonly used dowel pin designs and their respective sleeves, it is generally enough to lift the pin to a small distance of less than 1 mm and preferably only about 0.1 mm which would not disturb or warp the wax cast itself. Once lifted, the pin and the model die become loose and can be easily removed from the sleeve and hence the rest of the model by hand. Therefore, the method of consecutive loosening steps of each individual dowel pin would generally loosen the whole of the wax cast and allow for its further removal off the base of the model by hand. After that is accomplished, individual dies are easily removed from the wax cast.

In order to assist a dental technician in lifting each pin repeatedly by such a short distance, a model die ejector hand tool is proposed in the present invention. At one working end of the tool, a pushing rod is equipped with a short ejector shank extending therefrom for a distance of ejection, not exceeding 1 mm and preferably of about 0.1 mm in length. This design works well with one common design of the dowel pins in which the lower edge of the pin is made flush with the surface of the base. Since the diameter of the pushing rod is somewhat larger than the diameter of the dowel pin, the die ejector once positioned under the dowel pin and pushed toward it would limit the ejection distance of the pin by the length of the ejector shank. As a result, the pin would be lifted only by a very short distance which would only loosen it in its corresponding sleeve rather than move the whole die up which may cause a distortion of the wax cast.

In order to make the die ejector tool universal, the other end of the tool is designed to work with another type of widely used dowel pin and sleeve designs. In this design of the pin and sleeve combination, a removable cap is provided at the lower portion of the sleeve. Once the sleeve is positioned in the base model, the cap is removed allowing access to the lower end of the pin extending from the sleeve. In this design, the base does not surround the pin closely but the same general principle can still be applied by providing a die ejector with the pushing rod equipped at the working end with an ejector cavity of a predetermined diameter and depth. The diameter of the ejector cavity allows the pin to be accepted inside (the shape of the cavity may be somewhat tapered to repeat the shape of the pin if needed) and the depth is somewhat lower than the length of the pin extending from the sleeve. Pushing on the dowel pin with an ejector cavity of such design would lift the pin by a distance equal to the difference between the above mentioned pin length and the ejector cavity depth.

For a better understanding of the invention, its operating advantages and the specific objects attained by its uses, reference should be made to the accompanying drawings and descriptive matter in which there is illustrated a preferred embodiment of the present invention.

BRIEF DESCRIPTION OF THE DRAWINGS

A more complete appreciation of the subject matter of the present invention and the various advantages thereof can be realized by reference to the following detailed description in which reference is made to the accompanying drawing in which.

DETAILED DESCRIPTION OF THE MOST PREFERRED EMBODIMENT OF THE INVENTION

Figure 1:
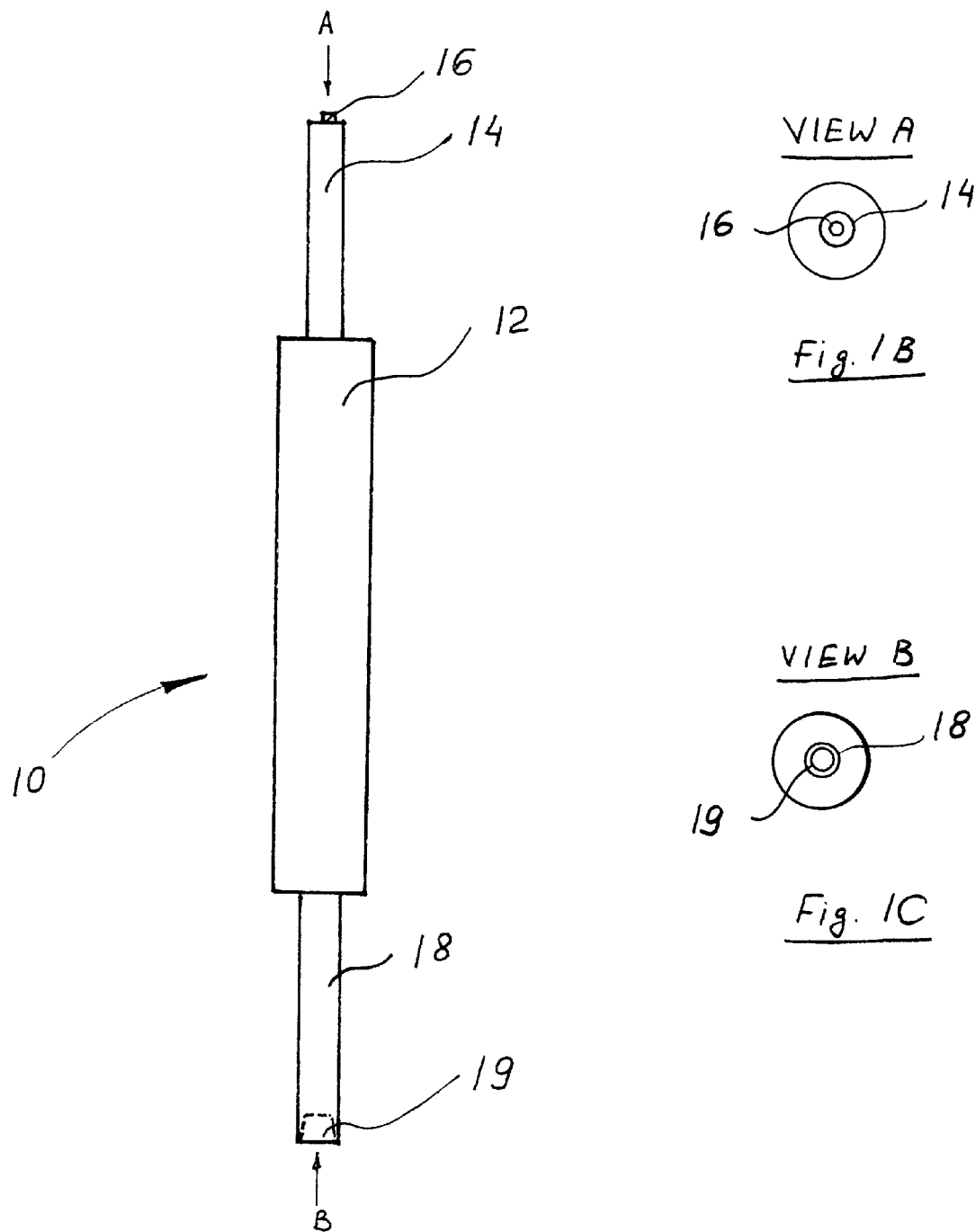
FIGS. 1A, 1B, and 1C are a general view of the model die ejector according to the present invention (FIG. 1A) accompanied by two axial views, view A (FIG. 1B) and view B (FIG. 1C).

A detailed description of the present invention follows with reference to accompanying drawings in which like elements are indicated by like reference numerals.

According to the present invention, a model die ejector tool is provided for limited distance lifting of a dowel pin from its respective sleeve. FIG. 1A illustrates a general view of the ejector (10) having a handle (12) and two pushing rods on both ends of the tool: a first pushing rod (14) and a second pushing rod (18). The first working end of the ejector containing the rushing rod (14) is designed to be used with one commonly used design of the dowel pin and sleeve combination in which the pin's lower edge is flush with the surface of the model base. In that case, the diameter of the pushing rod (14) is made slightly larger than the diameter of the dowel pin in order for the die ejector to abut against the sleeve or the model base surface. The axial view of the die ejector of this design is shown on view A of FIG. 1B. The end of the first pushing rod (14) is equipped with an ejector shank (16) designed to push on the lower edge of the dowel pin when engaged, to break the tight fit with the sleeve and therefore to loosen the model die in the model base without any substantial lifting thereof.

Figure 2:
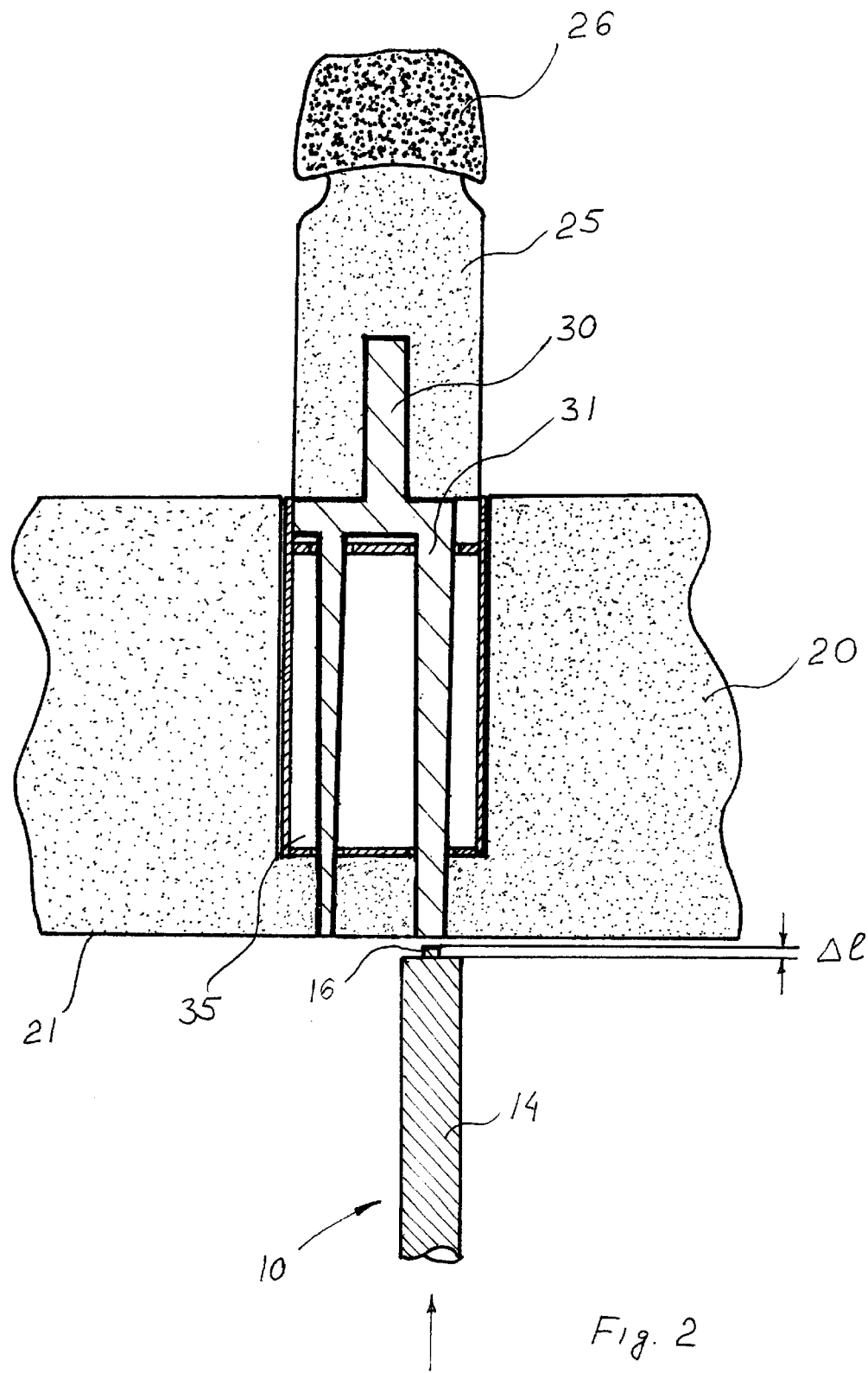
FIG. 2 is a highly schematic cross-sectional view of the die ejector tool used in a situation of the dowel pin lower edge being flush with the model base.

The operation of this portion of the die ejector (10) is shown schematically in more detail on FIG. 2. A dowel pin (30) is depicted firmly seated in its respective sleeve (35) permanently affixed at the gypsum model base (20). The dowel pin (30) is shown schematically as part of the model die (25) having on top a portion of the wax cast (26). The lower part of the dowel pin (30) contains a tapered pin member (31) seated in a corresponding opening of the sleeve (35) in such a way that the lower edge of the pin member (31) is flush with the lower surface (21) of the model base (20).

For loosening of the model die (25), the die ejector (10) is positioned under the dowel pin (30) so that the ejector shank (16) is aligned with the lower edge of the pin member (31). Pushing on the ejector (10) would lead to the ejector shank (16) pushing out the pin member (31) from its tight seat location in the sleeve (35). However, the distance of travel of the pin member (31) is limited to the length of the ejector shank (16) since the rod (14) would stop against the model base surface (21). That limitation of movement is critical since it would limit the action of the die ejector to only loosening the pin (30) in its position in the sleeve (35) rather than moving them apart for any considerable distance. Hence, the length Δl of the ejector shank (16) should be less than 1 mm and preferably about 0.1 mm to further limit any potential disturbance to the wax cast (26). It is preferred to design the pushing rod (14) having a diameter of about 3 mm, and the length of about 20 mm. In turn, the ejector shank (16) is preferred to have a diameter of about 1 mm and the length of about 0.1 mm.

Attention is called again to the FIG. 1A illustrating the second end of the die ejector designed to work in a similar way but with another widely used design of the dowel pin and sleeve combination. In this case, a removable cap is provided in the lower part of the sleeve so that when the model is hardened and the cap is removed, a space exists between the pin extending from the sleeve and the model base.

In that case, the second end of the model die ejector is designed to have a second pushing rod (18) of similar dimensions as the first pushing rod (14) and preferably having the diameter of about 3 mm and the length of about 20 mm. The end of the rod (18) is equipped with the cavity (19) designed to accept the portion of the dowel pin protruding from the sleeve. The axial view of this part of the model die ejector (10) is shown as view B on the FIG. 1C. The shape of the cavity (19) generally repeats the shape of the pin and may therefore have a generally tapered geometry if needed with an average diameter of about 2.5 mm. One of the critical dimensions of the cavity (19) is its depth. It should be chosen to be slightly less than the length of the protruding pin as would be appreciated from examining the FIG. 3 which shows the working relationship between the model die ejector and the dental model components. It is preferred to have this depth of about 2.5 mm.

Figure 3:
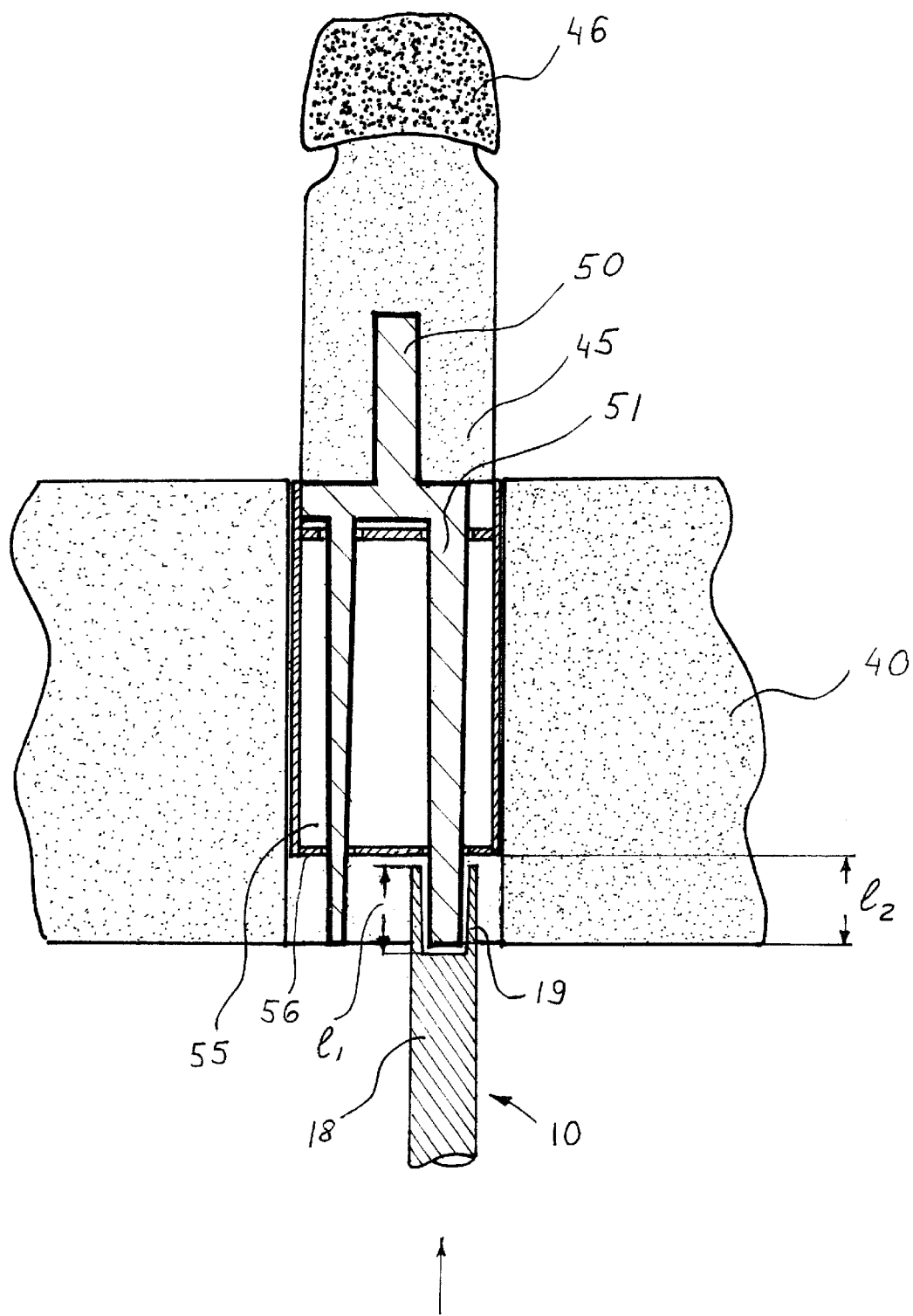
FIG. 3 is a highly schematic cross-sectional view of the die ejector tool used in a situation in which a sleeve cap is removed and the dowel pin extends beyond the sleeve lower surface while in a model base.

FIG. 3 depicts the arrangement of the dental model components showing the model base (40) containing the sleeve (55) which in turn houses a dowel pin (50) having a model die (45) extending from its upper part and terminating with a portion of the wax cast (46). The lower part of the pin (50) contains a tapered pin member (51) extending from the lower surface (56) of the sleeve (55) by the length $l_2$.

As was discussed above, the pushing rod (18) of the die ejector (10) contains an ejector cavity (19). The depth $l_1$ of that cavity is chosen to be slightly less than the length $l_2$ so that when the rod is used to push the pin member (51) from its seated position in the sleeve (55), the rod (18) abuts against the lower surface (56) of the sleeve (55) once the pin member (51) is moved for a distance equal the difference between these two lengths. It is important to have that difference being less than about 1 mm long and it is preferred to make it about 0.1 mm for the same reasons as discussed above.

As a result of applying a pushing force to the model die ejector, the dowel pin (50) would not move up in any significant way relative to its respective sleeve (55) but rather become loose in its seat. At the same time, the wax cast portion (46) would not be disturbed by these movements of the pin (50). The same procedure can be done with all other pins of the model (not shown) in a sequential manner in order to loosen them in their respective sleeves. Once that is accomplished, the whole wax cast containing all the model dies can be easily lifted off the base by hand for further removal of individual dies.

Although the present invention has been described with respect to a specific embodiment and application, it is not limited thereto. Numerous variations and modifications readily will be appreciated by those skilled in the art and are intended to be included within the scope of the present invention, which is recited in the following claims.

What I claim is:

1. A model die ejector for removing of a model die from a dental model base, said model base having a lower surface, said model die being mounted to the model base with a tapered dowel pin extending through the model base and having an exposed lower portion with a lower edge flush with said lower surface of said model base, said die ejector comprising:

a pushing rod having a working end, said pushing rod being larger in size at said working end than the size of the lower portion of the dowel pin, and an ejector shank for lifting the dowel pin off the dental model base for a predetermined limited distance, said ejector shank extending from the working end of said pushing rod, said ejector shank adapted to be engaged with said exposed lower portion of the dowel pin, said ejector shank being smaller in size than the size of said lower edge of the dowel pin, said ejector shank being smaller in size than the size of said lower edge of the dowel pin, said ejector shank having a length equal to said predetermined limited distance and being less than 1 mm, whereby said die ejector being capable of loosening said model die in its position on the dental model base for further easy separation and removal.

2. The model ejector as in claim 1, wherein said ejector shank has a length of about 0.1 mm.

3. The model die ejector as in claim 2, wherein said pushing rod being round and about 3 mm in diameter.

4. A model die ejector for removing of a model die from a dental model base, said model base containing a sleeve having a lower surface, said model die being mounted to the model base with a tapered dowel pin, said tapered dowel pin being housed by said sleeve and extending beyond said lower surface of the sleeve by a predetermined length, said die ejector comprising:

a pushing rod having a working end, said pushing rod being larger in size at said working end than the size of the lower portion of the dowel pin, and an ejector cavity positioned at the working end of the pushing rod and adapted to receive the lower portion of the dowel pin for lifting the dowel pin off the dental model base for a predetermined limited distance, the depth of the ejector cavity being determined as a difference between said predetermined length of the dowel pin extending beyond the sleeve and said predetermined limited distance, whereby said die ejector being capable of loosening said model die in its position on the dental model base for further easy separation and removal.

5. The model die ejector as in claim 4, wherein said predetermined limited distance being less than about 1 mm.

6. The model die ejector as in claim 5, wherein said predetermined limited distance being about 0.1 mm.

7. The model die ejector as in claim 2, wherein said pushing rod being round and about 3 mm in diameter.

8. The model die ejector as in claim 7, wherein said depth of the ejector cavity being about 2.5 mm.

9. The model die ejector as in claim 8, wherein said ejector cavity having an average diameter of about 2.5 mm.

10. A model die ejector for removing of a model die from a dental model base, said model die being mounted to the model base with a tapered dowel pin extending through the model base and having an exposed lower portion, said die ejector comprising:

a handle having a first end and a second end;

a first pushing rod extending from the first end of the handle and having a first working end, said first pushing rod being larger in size at said first working end than the size of said lower portion of the dowel pin;

an ejector shank for lifting the dowel pin off the dental model base for a predetermined limited distance, said ejector shank extending from the first working end of said first pushing rod, said ejector shank being smaller in size than the size of said lower portion of the dowel pin;

a second pushing rod extending from the second end of the handle and having a second working end, said second pushing rod being larger in size at said second working end than the size of said lower portion of the dowel pin; and an ejector cavity for lifting the dowel pin, said ejector cavity positioned at said second working end of the second pushing rod, said ejector cavity adapted to receive the lower portion of the dowel pin, the depth of the ejector cavity being sufficient for lifting the dowel pin off the dental model base for said predetermined limited distance, whereby said die ejector being capable of loosening said model die in its position on the dental model base for further easy separation and removal.

11. The model die ejector as in claim 10, wherein said predetermined limited distance being less than 1 mm.

12. The model die ejector as in claim 11, wherein said predetermined limited distance being about 0.1 mm.

13. The model die ejector as in claim 12, wherein both the first and the second pushing rods being round and having a diameter of about 3 mm.

14. The model die ejector as in claim 13, wherein the depth of said ejector cavity being about 2.5 mm.

\* \* \* \* \*